(12) United States Patent
Chen et al.

(10) Patent No.: US 12,428,402 B2
(45) Date of Patent: Sep. 30, 2025

(54) RESMETIROM CRYSTAL, PREPARATION METHOD FOR SAME, AND USES THEREOF

(71) Applicant: CRYSTAL PHARMACEUTICAL (SUZHOU) CO., LTD., Suzhou (CN)

(72) Inventors: Minhua Chen, Suzhou (CN); Xingjuan Chang, Suzhou (CN)

(73) Assignee: CRYSTAL PHARMACEUTICAL (SUZHOU) CO., LTD., Suzhou (CN)

( * ) Notice: Subject to any disclaimer, the term of this patent is extended or adjusted under 35 U.S.C. 154(b) by 692 days.

(21) Appl. No.: 17/849,281

(22) Filed: Jun. 24, 2022

(65) Prior Publication Data

US 2022/0372021 A1 Nov. 24, 2022

Related U.S. Application Data

(63) Continuation of application No. PCT/CN2020/136551, filed on Dec. 15, 2020.

(30) Foreign Application Priority Data

Dec. 26, 2019 (CN) .......................... 201911366681.2
Dec. 26, 2019 (CN) .......................... 201911369416.X
Apr. 16, 2020 (CN) .......................... 202010300436.8

(51) Int. Cl.
C07D 403/12 (2006.01)

(52) U.S. Cl.
CPC ........ C07D 403/12 (2013.01); *C07B 2200/13* (2013.01)

(58) Field of Classification Search
None
See application file for complete search history.

(56) References Cited

FOREIGN PATENT DOCUMENTS

| CN | 101228135 | 7/2008 |
|---|---|---|
| CN | 105008335 | 10/2015 |
| WO | WO 2020/010068 | 1/2020 |
| WO | WO 2020/073974 | 4/2020 |
| WO | WO 2020/227549 | 11/2020 |

OTHER PUBLICATIONS

Kelly et al., "Discovery of 2-[3,5-Dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a Highly Selective Thyroid Hormone Receptor β Agonist in Clinical Trials for the Treatment of Dyslipidemia" *J. Med. Chem.* 2014, 57, 3912-3923.
International Search Report and Written Opinion issued in Corresponding PCT Application No. PCT/CN2020/136551, dated Mar. 12, 2021 (English Translation provided).

*Primary Examiner* — Po-Chih Chen
(74) *Attorney, Agent, or Firm* — NORTON ROSE FULBRIGHT US LLP (57) ABSTRACT

Novel crystalline forms of Resmetirom (Referred to as "Compound I"), and preparation methods thereof, pharmaceutical compositions containing the crystalline forms, and uses of the crystalline forms for preparing THR-β selective agonist drugs and drugs for treating NASH and HeFH. Compared with prior arts, the provided crystalline forms of Compound I have one or more improved properties, which is of great value to the optimization and development of the drugs containing Compound I.

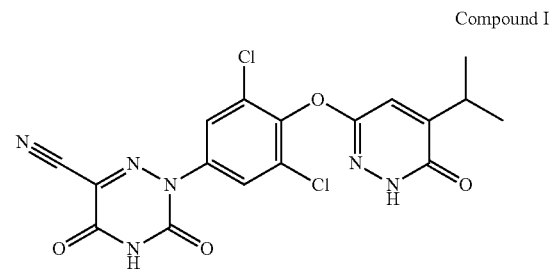

Compound I

9 Claims, 6 Drawing Sheets

RESMETIROM CRYSTAL, PREPARATION METHOD FOR SAME, AND USES THEREOF

CROSS REFERENCE TO RELATED APPLICATIONS

The present application is a continuation application of International Application No. PCT/CN2020/136551, filed Dec. 15, 2020, which claims the benefit of priority to Chinese patent application No. 201911369416.X, filed with the China National Intellectual Property Administration on Dec. 26, 2019, Chinese patent application No. 201911366681.2, filed with the China National Intellectual Property Administration on Dec. 26, 2019, and Chinese patent application No. 202010300436.8, filed with the China National Intellectual Property Administration on Apr. 16, 2020. The contents of each of the referenced applications are incorporated into the present application by reference.

TECHNICAL FIELD

The present disclosure pertains to the field of chemical crystallography, particularly relates to crystalline forms of Resmetirom, processes for preparation and use thereof.

BACKGROUND

Heterozygous Familial Hypercholesterolemia (HeFH) is one of the most serious disorders of lipid metabolism and can lead to various life-threatening complications of cardiovascular disease. Non-alcoholic steatohepatitis (NASH) is a severe liver disease with steatosis accompanied by inflammation and hepatocellular injury. Resmetirom as a thyroid hormone receptor β (THR-β) selective agonist, can ameliorate the symptoms of NASH and HeFH by reducing LDL cholesterol, triglyceride and hepatic fat levels, and stimulating hepatic mitochondrial biosynthesis in individuals with NASH. Resmetirom has achieved positive results in Phase II clinical trials of NASH and HeFH.

The chemical name of Resmetirom is 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile (hereinafter referred to as "Compound I"), and the structure is shown as follows:

Compound I

A crystalline form is a solid material whose constituents are arranged in a highly ordered microscopic structure, forming a crystal lattice that extends in all directions. Polymorphism refers to the phenomenon that a compound exists in two or more than two crystalline forms. Different crystalline forms have different physicochemical properties and can affect drug's in vivo dissolution and absorption, which further affect drug's clinical efficacy and safety to some extent. In particular, for poorly soluble drugs, the effects of crystalline forms will be greater. Therefore, drug polymorphism is an important part of drug research and drug quality control.

A hydrate, an anhydrous crystalline form I, a methyl isobutyl ketone solvate, and a dimethylacetamide solvate of Compound I were disclosed in U.S. Pat. No. 9,266,861B2. Among them, the methyl isobutyl ketone solvate and the dimethylacetamide solvate are not suitable for medicinal use as methyl isobutyl ketone and dimethylacetamide are toxic organic solvents. The HPLC purity of the hydrate disclosed in U.S. Pat. No. 9,266,861B2 is 96.4%. The high impurity content will affect the appearance and stability of the drug products and further increase the toxicity. Crystalline form I is the best solid form of Compound I among the known solid forms with the melting point (onset temperature) of about 321° C. However, the preparation of crystalline form I is complicated and specific starting materials, such as methyl isobutyl ketone solvate and dimethyl acetamide solvate are required. The inventors of the present disclosure repeated the preparation method disclosed in U.S. Pat. No. 9,266,861B2 to obtain crystalline form I and conducted characterizations. The results show that crystalline form I has low solubility, poor stability upon grinding, and poor compressibility. Therefore, it is still necessary to develop a crystalline form of Compound I with high solubility, good physicochemical stability, safety and non-toxicity, and good physicochemical properties, for the development of drugs containing Compound I.

In order to overcome the shortcomings of prior arts, the inventors of the present disclosure have conducted a lot of experimental studies on Compound I in an attempt to obtain a crystalline form that is more suitable for medicinal use. More than 300 experiments have been conducted, but most of the obtained solids were solvates of Compound I, such as methanol solvate, acetone solvate, tetrahydrofuran solvate, chlorobenzene solvate, toluene solvate and cyclohexanone solvate. The inventors of the present disclosure found that Compound I easily combine with solvents to form solvates, and it is very difficult to obtain a stable non-solvate of Compound I.

The inventors of the present disclosure have put a lot of creative work in order to obtain crystalline forms CSIV and CSV, which have advantages in physiochemical properties, formulation processability, bioavailability, etc. For example, crystalline forms CSIV and CSV of Compound I have advantages in at least one aspect of melting point, solubility, hygroscopicity, purification ability, stability, adhesiveness, compressibility, flowability, in vitro and in vivo dissolution, and bioavailability, etc. In particular, crystalline forms CSIV and CSV have high solubility, good physicochemical stability, low hygroscopicity, good mechanical stability and good compressibility, which solve the problems existing in prior arts and are of great significance for the development of drugs containing Compound I.

SUMMARY

The main objective of the present disclosure is to provide novel crystalline forms of Compound I, preparation method and use thereof.

According to the objective of the present disclosure, crystalline form CSIV of Compound I is provided (hereinafter referred to as "Form CSIV").

In one aspect provided herein, the X-ray powder diffraction pattern of Form CSIV comprises characteristic peaks at 2theta values of 6.3°±0.2°, 18.1°±0.2° and 25.3°±0.2° using CuKα radiation.

Furthermore, the X-ray powder diffraction pattern of Form CSIV comprises one or two or three characteristic peaks at 2theta values of 10.4°±0.2°, 20.6°±0.2° and 24.6°±0.2° using CuKα radiation. Preferably, the X-ray powder diffraction pattern of Form CSIV comprises three characteristic peaks at 2theta values of 10.4°±0.2°, 20.6°±0.2° and 24.6°±0.2° using CuKα radiation.

Furthermore, the X-ray powder diffraction pattern of Form CSIV comprises one or two characteristic peaks at 2theta values of 14.5°±0.2° and 28.6°±0.2° using CuKα radiation. Preferably, the X-ray powder diffraction pattern of Form CSIV comprises two characteristic peaks at 2theta values of 14.5°±0.2° and 28.6°±0.2° using CuKα radiation.

In another aspect provided herein, the X-ray powder diffraction pattern of Form CSIV comprises three or four or five or six or seven or eight characteristic peaks at 2theta values of 6.3°±0.2°, 18.1°±0.2°, 25.3°±0.2°, 10.4°±0.2°, 20.6°±0.2°, 24.6°±0.2°, 14.5°±0.2° and 28.6°±0.2° using CuKα radiation.

Figure 1:
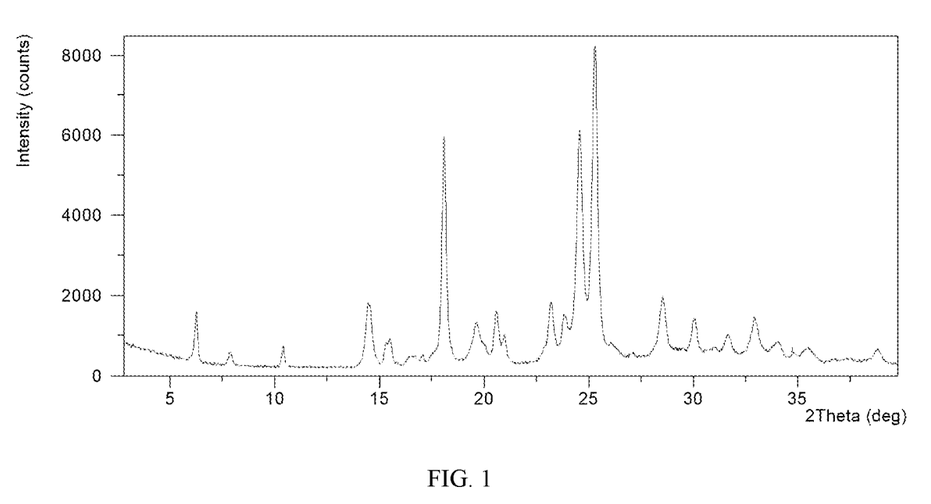
FIG. 1 shows an XRPD pattern of Form CSIV in Example 1

Without any limitation being implied, the X-ray powder diffraction pattern of Form CSIV is substantially as depicted in FIG. 1.

Figure 2:
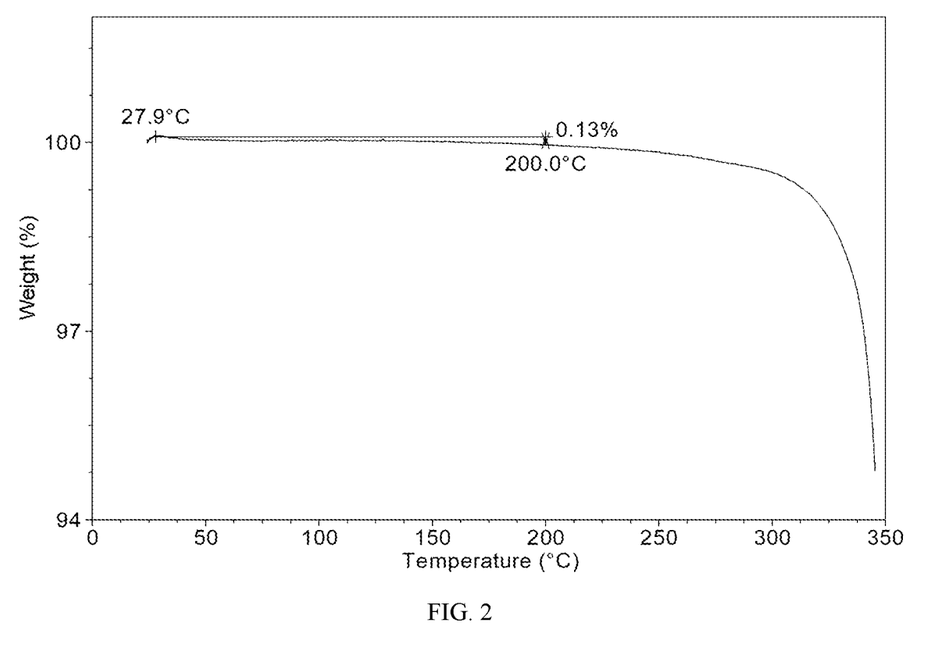
FIG. 2 shows a TGA curve of Form CSIV in Example 1

Without any limitation being implied, the Thermo Gravimetric Analysis (TGA) curve of Form CSIV is substantially as depicted in FIG. 2, which shows about 0.1% weight loss when heated to 200° C.

Without any limitation being implied, Form CSIV is an anhydrate.

Figure 3:
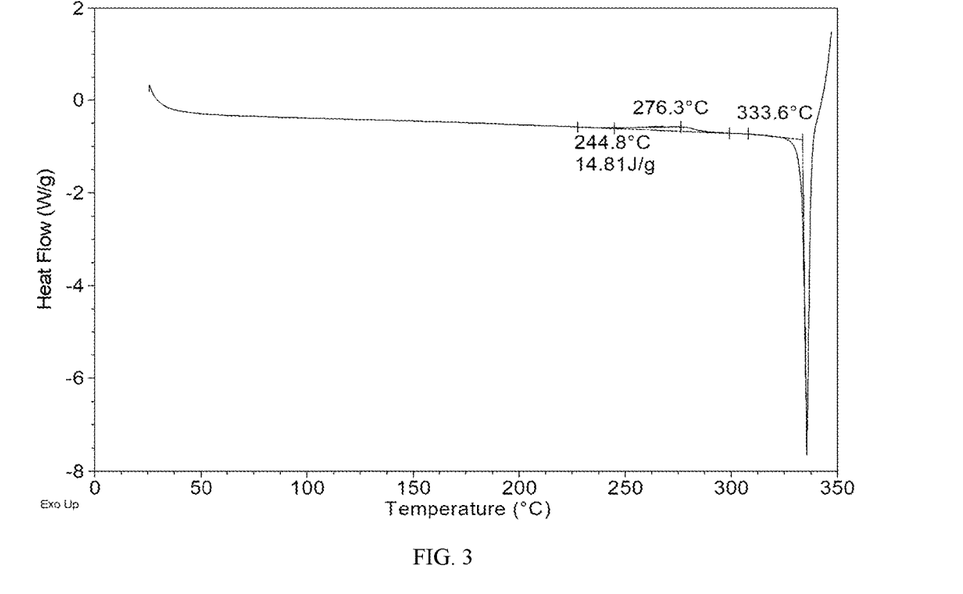
FIG. 3 shows a DSC curve of Form CSIV in Example 1

Without any limitation being implied, the Differential Scanning calorimetry (DSC) curve of Form CSIV is substantially as depicted in FIG. 3, which shows an exothermic peak at around 245° C. (onset temperature) corresponding to crystalline transformation, and an endothermic peak at around 334° C. (onset temperature) corresponding to melting.

According to the objective of the present disclosure, a process for preparing Form CSIV is also provided. The process comprises: stirring Compound I solid in a nitrile, separating the solid and drying to obtain Form CSIV.

Furthermore, said nitrile is preferably a C2-C4 nitrile.

Furthermore, said nitrile is preferably acetonitrile; said stirring temperature is preferably −20-30° C., further preferably room temperature; said drying temperature is preferably 20-100° C., further preferably 50° C.-100° C.

According to the objective of the present disclosure, crystalline form CSV of Compound I is provided (hereinafter referred to as "Form CSV").

In one aspect provided herein, the X-ray powder diffraction pattern of Form CSV comprises characteristic peaks at 2theta values of 11.9°±0.2°, 13.8°±0.2° and 17.3°±0.2° using CuKα radiation.

Furthermore, the X-ray powder diffraction pattern of Form CSV comprises one or two or three characteristic peaks at 2theta values of 19.9°±0.2°, 21.2°±0.2° and 26.2±0.2° using CuKα radiation. Preferably, the X-ray powder diffraction pattern of Form CSV comprises three characteristic peaks at 2theta values of 19.9°±0.2°, 21.2°±0.2° and 26.2±0.2° using CuKα radiation.

Furthermore, the X-ray powder diffraction pattern of Form CSV comprises one or two or three characteristic peaks at 2theta values of 20.8°±0.2°, 24.5°±0.2° and 27.0°±0.2° using CuKα radiation. Preferably, the X-ray powder diffraction pattern of Form CSV comprises three characteristic peaks at 2theta values of 20.8°±0.2°, 24.5°±0.2° and 27.0°±0.2° using CuKα radiation.

In another aspect provided herein, the X-ray powder diffraction pattern of Form CSV comprises three or four or five or six or seven or eight or nine or ten or eleven or twelve or thirteen characteristic peaks at 2theta values of 11.9°±0.2°, 13.8°±0.2°, 17.3°±0.2°, 19.9°±0.2°, 21.2°±0.2°, 26.2±0.2°, 20.8°±0.2°, 24.5°±0.2°, 27.0°±0.2°, 10.6°±0.2°, 18.6±0.2°, 19.6°±0.2° and 28.5°±0.2° using CuKα radiation.

Figure 4:
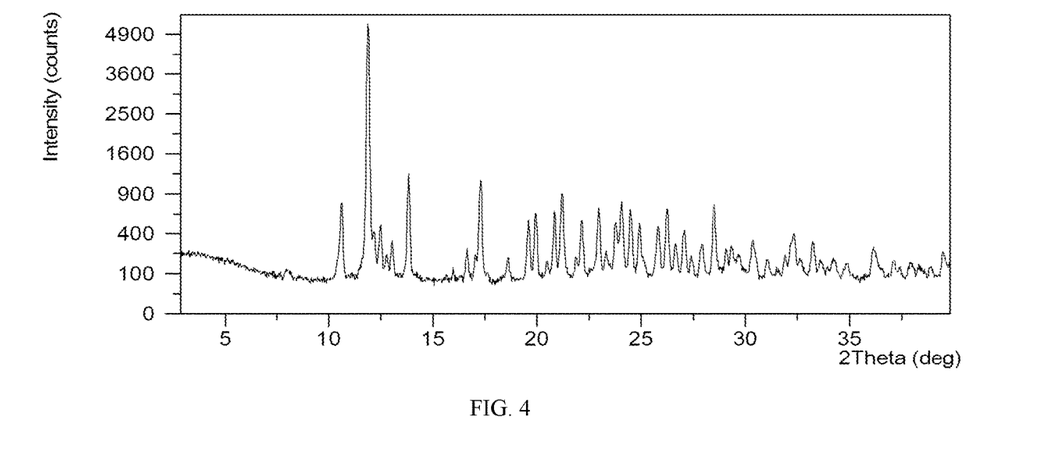
FIG. 4 shows an XRPD pattern of Form CSV in Example 3

Without any limitation being implied, the X-ray powder diffraction pattern of Form CSV is substantially as depicted in FIG. 4.

Without any limitation being implied, Form CSV is an anhydrate.

According to the objective of the present disclosure, a process for preparing Form CSV is also provided. The process comprises:
 step 1: stirring Compound I solid in dimethyl carbonate, separating the solid and drying;
 step 2: stirring the obtained solid in an alcohol and then separating to obtain Form CSV.

Furthermore, said alcohol is a C2-C8 alcohol.

Furthermore, said stirring temperature in step 1 is preferably −20-50° C., said drying temperature is preferably 20-60° C., said stirring time in step 2 is preferably 0.5 hours-3 days, said stirring temperature in step 2 is preferably −20-30° C.

Form CSIV of the present disclosure has the following advantages:

(1) Compared with prior arts, Form CSIV of the present disclosure has higher solubility. Particularly after being equilibrated for 1 hour and 24 hours in Simulated Gastric Fluid (SGF), the solubility of Form CSIV are 10.6 and 5.0 times that of Form I, respectively.

Compound I is a poorly water-soluble drug. Higher solubility is beneficial to improve drug's in vivo absorption and bioavailability, thus improving drug efficacy. In addition, drug dose reduction without affecting efficacy is possible due to higher solubility, thereby reducing the drug's side effects and improving drug safety.

(2) Form CSIV drug substance of the present disclosure has good physicochemical and mechanical stability. Crystalline state of Form CSIV drug substance doesn't change for at least 6 months when stored under 25° C./60% relative humidity (RH) with sealed condition. The chemical purity is above 99.7% and remains substantially unchanged during storage.

Crystalline state of Form CSIV drug substance doesn't change for at least 6 months when stored under 40° C./75% RH with sealed condition. Crystalline state of Form CSIV drug substance doesn't change for at least 1 month when stored under 60° C./75% RH with sealed condition, and the chemical purity is above 99.7% and remains substantially unchanged during storage. These results show that Form CSIV drug substance has good stability under accelerated and stress conditions. Drug substance will go through high temperature and high humidity conditions caused by different season, regional climate and environment during storage, transportation, and manufacturing processes. Therefore, good stability under accelerated and stress conditions is of great importance to the drug development. Form CSIV drug substance has good stability under stress conditions, which is beneficial to avoid the influence on drug quality when not stored in condition recommended in label.

Crystal transformation can lead to changes in the absorption of the drug, affect bioavailability, and even cause toxicity and side effects. Good chemical stability of drug substance ensure that no impurities are generated during production and storage. Form CSIV has good physical stability, ensuring consistent and controllable quality of the drug substance and drug product, minimizing quality change, bioavailability change and toxicity due to crystal transformation or impurity generation.

(3) Form CSIV of the present disclosure has low hygroscopicity. The test results show that the weight gain of Form CSIV at 25° C./80% RH is 0.58%, indication that Form CSIV is slightly hygroscopic.

Hygroscopicity affects the physicochemical stability of the drug directly, as high hygroscopicity tends to cause chemical degradation and crystal transformation. In addition, high hygroscopicity will reduce the flowability of the drug, thereby affecting the processing of the drug. Moreover, drug substances with high hygroscopicity require low humidity environment during production and storage, which puts strict requirements on production and imposes higher costs. More importantly, high hygroscopicity is likely to cause variation in the content of active pharmaceutical ingredients in the drug, thus affecting drug quality. The crystalline form with low hygroscopicity is not demanding on the environment, which reduces the cost of production, storage and quality control, and has strong economic values.

(4) Compared with prior arts, Form CSIV of the present disclosure has better compressibility. Failure in hardness/friability test and tablet crack issue can be avoided due to better compressibility of Form CSIV, making the preparation process more reliable, improving product appearance, promoting product quality and production efficiency. Better compressibility can increase the compression rate, further increase the efficiency of process, and reduce the cost of compressibility improving excipients.

Form CSV of the present disclosure has the following advantages:

(1) Compared with prior arts, Form CSV of the present disclosure has a higher solubility. Particularly after being equilibrated for 1 hour and 24 hours in SGF, the solubility of Form CSV are 7.1 and 8.7 times that of Form I, respectively.

Compound I is a poorly water-soluble drug. Higher solubility is beneficial to improve drug's in vivo absorption and bioavailability, thus improving drug efficacy. In addition, drug dose reduction without affecting efficacy is possible due to higher solubility, thereby reducing the drug's side effects and improving drug safety.

(2) Form CSV drug substance of the present disclosure has good physicochemical and mechanical stability. Crystalline state of Form CSV drug substance doesn't change for at least one month when stored under 40° C./75% RH with sealed condition. The crystalline form of Form CSV drug substance doesn't change for at least one week when stored under 60° C./75% RH with open and sealed condition. The chemical purity is above 99.8% and remains substantially unchanged during storage. These results show that Form CSV drug substance has good stability under accelerated and stress conditions. Drug substance will go through high temperature and high humidity conditions caused by different season, regional climate and environment during storage, transportation, and manufacturing processes. Therefore, good stability under accelerated and stress conditions is of great importance to the drug development. Form CSV drug substance has good stability under stress conditions, which is beneficial to avoid the influence on drug quality when not stored in condition recommended in label.

Meanwhile, compared with prior arts, Form CSV has good mechanical stability. Crystalline state of Form CSV drug substance doesn't change after grinding. Form CSV drug substance has good physical stability. However, Form I transforms into amorphous after grinding, and the crystalline state changes. Grinding and pulverization are often required in the drug manufacturing process. Good physical stability of the drug substance can reduce the risk of crystallinity decrease and crystal transformation during the drug production process.

Crystal transformation can lead to changes in the absorption of the drug, affect bioavailability, and even cause toxicity and side effects. Good chemical stability of drug substance ensure that no impurities are generated during production and storage. Form CSV has good physical stability, ensuring consistent and controllable quality of the drug substance and drug product, minimizing quality change, bioavailability change and toxicity due to crystal transformation or impurity generation.

(3) Form CSV has low hygroscopicity. The test results show that the weight gain of Form CSV at 25° C./80% RH is 0.13%, indicating that Form CSV is non hygroscopic or almost non-hygroscopic.

Hygroscopicity affects the physicochemical stability of the drug directly, as high hygroscopicity tends to cause chemical degradation and crystal transformation. In addition, high hygroscopicity will reduce the flowability of the drug, thereby affecting the processing of the drug. Moreover, drug substances with high hygroscopicity require low humidity environment during production and storage, which puts strict requirements on production and imposes higher costs. More importantly, high hygroscopicity is likely to cause variation in the content of active pharmaceutical ingredients in the drug, thus affecting drug quality. The crystalline form with low hygroscopicity is not demanding on the environment, which reduces the cost of production, storage and quality control, and has strong economic values.

According to the objective of the present disclosure, a pharmaceutical composition is provided, said pharmaceutical composition comprises a therapeutically effective amount of Form CSIV or Form CSV or combinations thereof and pharmaceutically acceptable excipients.

Furthermore, Form CSIV or Form CSV or combinations thereof can be used for preparing THR-β selective agonist drugs.

Furthermore, Form CSIV or Form CSV or combinations thereof can be used for preparing drugs treating NASH and HeFH.

In the present disclosure, said "stirring" is accomplished by using a conventional method in the field such as magnetic stirring or mechanical stirring and the stirring speed is 50 to 1800 r/min. Preferably the magnetic stirring speed is 300 to 900 r/min and mechanical stirring speed is 100 to 300 r/min.

Said "separation" is accomplished by using a conventional method in the field such as centrifugation or filtration. The operation of "centrifugation" is as follows: the sample to be separated is placed into the centrifuge tube, and then centrifuged at a rate of 10000 r/min until the solid all sink to the bottom of the tube.

Said "drying" is accomplished at room temperature or higher. The drying temperature is from room temperature to about 60° C. Drying is accomplished in a fume hood, forced air convection oven or vacuum oven.

In the present disclosure, "crystal" or "crystalline form" refers to the solids being identified by the X-ray diffraction pattern. Those skilled in the art are able to understand that physicochemical properties discussed herein can be characterized. The experimental errors depend on the instrument conditions, the sample preparation and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions. Therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be considered. An error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have exactly the same X-ray diffraction pattern of the example shown herein. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, CSIV and CSV of the present disclosure are pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and furthermore specifically less than 1% (w/w).

In the present disclosure, the term "about" when referring to a measurable value such as weight, time, temperature, and the like, is meant to encompass variations of ±10%, ±5%, ±1%, ±0.5%, or even ±0.1% of the specified amount.

DETAILED DESCRIPTION

The present disclosure is further illustrated by the following examples which describe the preparation and use of the crystalline forms of the present disclosure in detail. It is obvious to those skilled in the art that changes in the materials and methods can be accomplished without departing from the scope of the present disclosure.

The abbreviations used in the present disclosure are explained as follows:
XRPD: X-ray Powder Diffraction
DSC: Differential Scanning calorimetry
TGA: Thermo Gravimetric Analysis
DVS: Dynamic Vapor Sorption
$^1$H NMR: Proton Nuclear Magnetic Resonance
HPLC: High Performance Liquid Chromatography Instruments and Methods Used for Data Collection X-ray powder diffraction patterns in the present disclosure were acquired by a Bruker D2 PHASER X-ray powder diffractometer. The parameters of the X-ray powder diffraction method of the present disclosure are as follows:
X-Ray source: Cu, Kα
Kα1 (Å): 1.54060; Kα2 (Å): 1.54439
Kα2/Kα1 intensity ratio: 0.50
Voltage: 30 (kV)
Current: 10 (mA)
Scan range (2θ): from 3.0 degree to 40.0 degree Differential scanning calorimetry (DSC) data in the present disclosure were acquired by a TA Q2000. The parameters of the DSC method of the present disclosure are as follows:
Heating rate: 10° C./min
Purge gas: nitrogen Thermo gravimetric analysis (TGA) data in the present disclosure were acquired by a TA Q500. The parameters of the TGA method of the present disclosure are as follows:
Heating rate: 10° C./min
Purge gas: nitrogen Dynamic Vapor Sorption (DVS) was measured via an SMS (Surface Measurement Systems Ltd.) intrinsic DVS instrument. Typical Parameters for DVS test are as follows:
Temperature: 25° C.
Gas and flow rate: N$_2$, 200 mL/min
RH range: 0% RH to 95% RH Proton nuclear magnetic resonance spectrum data ($^1$H NMR) were collected from a Bruker Avance II DMX 400M HZ NMR spectrometer. 1-5 mg of sample was weighed and dissolved in 0.5 mL of deuterated dimethyl sulfoxide to obtain a solution with a concentration of 2-10 mg/mL.

The parameters for related substance detection by HPLC in the present disclosure are shown in Table 1.

TABLE 1

| UPLC | Waters UPLC H-Class plus | |
|---|---|---|
| Column | Waters ACQUITY UPLC BEH C18, 2.1 mm*50 mm, 1.7 μm | |
| Mobile Phase | A: 0.1% Trifluoroacetic acid (TFA) in H$_2$O<br>B : 0.1% TFA in Acetonitrile | |
| Gradient | Time (min) | % B |
| | 0.00 | 10 |
| | 0.50 | 10 |
| | 2.50 | 50 |
| | 6.50 | 90 |
| | 8.00 | 90 |
| | 8.10 | 10 |
| | 10.00 | 10 |
| Run time | 10 min | |
| Stop time | 0 min | |
| Flow rate | 0.5 mL/min | |

TABLE 1-continued

| | |
|---|---|
| Injection Volume | 1 μL |
| Detector wavelength | 215 nm |
| Column Temperature | 40° C. |
| Sample Temperature | Room Temperature |
| Diluent | Acetonitrile: H$_2$O = 1:1(v/v) |

Unless otherwise specified, the following examples were conducted at room temperature. Said "room temperature" is not a specific temperature, but a temperature range of 10-30° C.

According to the present disclosure, Compound I and/or its salt used as raw materials include, but are not limited to solid (crystalline and amorphous), semisolid, wax, oil, liquid form or solution. Preferably, Compound I and/or its salt used as a raw material is a solid.

Compound I used in the following examples can be prepared by known methods in the prior arts, for example, the method disclosed in WO2014043706A1.

EXAMPLES

Example 1: Preparation of Form CSIV 145.2 mg of Compound I solid was weighed into a glass vial. 1.5 mL of acetonitrile was added, and then stirred at room temperature for three days to form a suspension. The suspension was centrifuged to obtain a solid. The obtained solid was dried under vacuum at 100° C. for 3.5 hours to obtain Form CSIV.

The XRPD pattern of Form CSIV obtained in this example is shown in FIG. 1, and the XRPD data are listed in Table 2.

The TGA curve of Form CSIV is substantially as depicted in FIG. 2, which shows about 0.1% weight loss when heated to 200° C.

The DSC curve of Form CSIV is substantially as depicted in FIG. 3, which shows an exothermic peak and an endothermic peak. The peak at around 245° C. (onset temperature) is an exothermic peak of crystal transformation, and the endothermic peak at around 334° C. (onset temperature) corresponds to melting.

The $^1$H NMR data of Form CSIV are: $^1$H NMR (400 MHz, DMSO-d6) δ 13.29 (s, 1H), 12.24 (s, 1H), 7.78 (s, 2H), 7.45 (s, 1H), 3.05 (m, 1H), 1.20 (d, J=6.9 Hz, 6H)

TABLE 2

| 2θ (°) | d spacing (Å) | Relative intensity % |
|---|---|---|
| 6.26 | 14.13 | 15.68 |
| 7.88 | 11.21 | 3.93 |
| 10.40 | 8.50 | 6.46 |
| 14.48 | 6.12 | 19.94 |
| 14.57 | 6.08 | 18.19 |
| 15.32 | 5.78 | 7.55 |
| 15.51 | 5.72 | 8.63 |
| 16.39 | 5.41 | 2.88 |
| 17.08 | 5.19 | 3.69 |
| 18.10 | 4.90 | 71.67 |
| 19.65 | 4.52 | 13.55 |
| 20.60 | 4.31 | 17.34 |
| 20.98 | 4.23 | 10.25 |
| 23.21 | 3.83 | 20.11 |
| 23.85 | 3.73 | 16.01 |
| 24.58 | 3.62 | 74.11 |
| 25.31 | 3.52 | 100.00 |
| 26.08 | 3.42 | 7.51 |
| 27.11 | 3.29 | 4.29 |
| 28.55 | 3.13 | 21.78 |
| 30.05 | 2.97 | 14.73 |
| 31.02 | 2.88 | 6.02 |
| 31.67 | 2.83 | 10.20 |
| 32.94 | 2.72 | 14.56 |
| 34.03 | 2.63 | 7.50 |
| 34.76 | 2.58 | 5.80 |
| 35.50 | 2.53 | 5.77 |
| 36.76 | 2.45 | 2.33 |
| 37.43 | 2.40 | 2.42 |
| 38.80 | 2.32 | 5.18 |

Example 2: Preparation of Form CSIV

A certain amount of Compound I solid was put in 30 mL of acetonitrile and stirred at −20° C. for about 37.5 h. The obtained solid was separated and dried under vacuum at 50° C. for about 23.5 h to obtain Form CSIV of the present disclosure.

Example 3: Preparation of Form CSV 2.0742 g of Compound I solid was weighed into a glass vial, 30 mL of dimethyl carbonate was added, and then stirred at 5° C. for 19 hours to form a suspension. The suspension was centrifugated and the separated solid was dried under vacuum at 50° C. for 4 hours to obtain a dry solid. 54.9 mg of the dry solid was weighed into a glass vial, 1 mL of isopropyl alcohol was added, and then stirred at 5° C. for 1.5 hours to obtain Form CSV.

The XRPD pattern of Form CSV obtained in this example is shown in FIG. 4, and the XRPD data are listed in Table 3.

Figure 5:
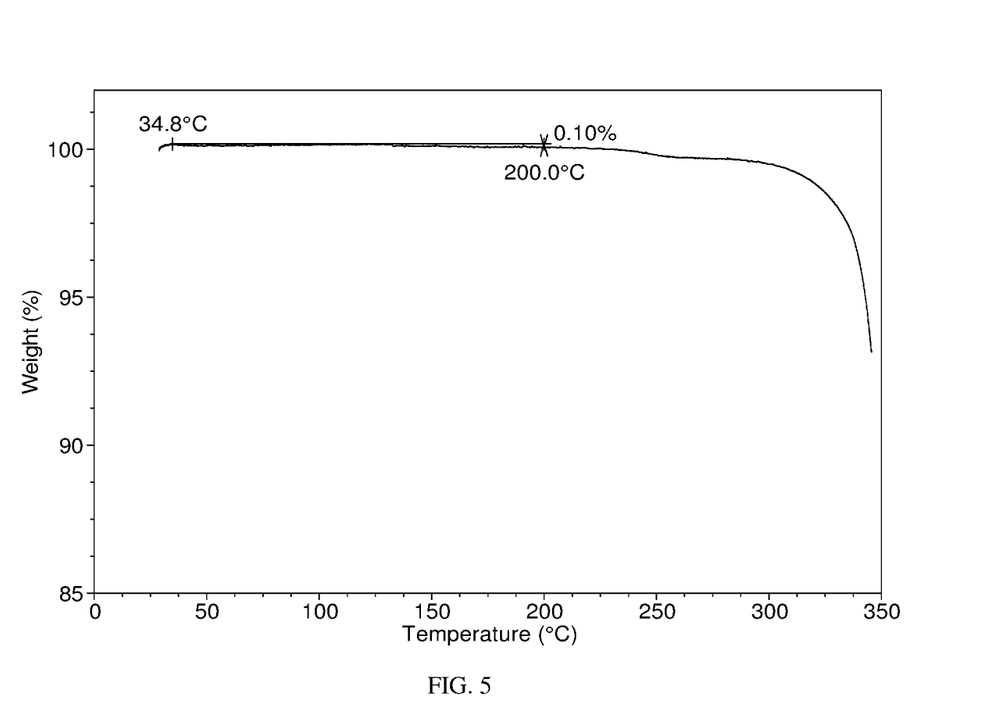
FIG. 5 shows a TGA curve of Form CSV in Example 3

The TGA curve of Form CSV is substantially as depicted in FIG. 5, which shows about 0.1% weight loss when heated to 200° C.

The $^1$H NMR data of Form CSV are: $^1$H NMR (400 MHz, DMSO-d6) δ 13.29 (s, 1H), 12.25 (s, 1H), 7.79 (s, 2H), 7.45 (s, 1H), 3.05 (m, 1H), 1.20 (d, J=6.9 Hz, 6H)

TABLE 3

| 2θ (°) | d spacing (Å) | Relative intensity % |
|---|---|---|
| 10.61 | 8.34 | 13.46 |
| 11.88 | 7.45 | 100.00 |
| 12.47 | 7.10 | 8.14 |
| 13.03 | 6.79 | 5.05 |
| 13.83 | 6.41 | 22.15 |
| 16.63 | 5.33 | 3.82 |
| 17.27 | 5.13 | 20.20 |
| 18.61 | 4.77 | 2.21 |
| 19.59 | 4.53 | 9.14 |
| 19.94 | 4.45 | 10.80 |
| 20.85 | 4.26 | 11.12 |
| 21.20 | 4.19 | 16.07 |
| 22.15 | 4.01 | 8.96 |
| 22.97 | 3.87 | 12.28 |
| 23.77 | 3.74 | 8.66 |
| 24.06 | 3.70 | 13.65 |
| 24.49 | 3.64 | 10.51 |
| 24.92 | 3.57 | 8.42 |
| 25.82 | 3.45 | 7.83 |

TABLE 3-continued

| 2θ (°) | d spacing (Å) | Relative intensity % |
|---|---|---|
| 26.24 | 3.40 | 11.66 |
| 26.64 | 3.35 | 4.46 |
| 27.05 | 3.30 | 6.36 |
| 27.41 | 3.25 | 2.39 |
| 27.91 | 3.20 | 4.26 |
| 28.50 | 3.13 | 12.48 |
| 29.10 | 3.07 | 3.56 |
| 29.36 | 3.04 | 4.07 |
| 30.38 | 2.94 | 4.99 |
| 31.07 | 2.88 | 2.13 |
| 32.33 | 2.77 | 6.22 |
| 33.25 | 2.69 | 4.77 |
| 34.24 | 2.62 | 2.21 |
| 36.17 | 2.48 | 3.66 |
| 37.13 | 2.42 | 2.11 |
| 37.96 | 2.37 | 1.65 |
| 39.54 | 2.28 | 3.02 |

Example 4 Preparation of Form CSV 498.8 mg of Compound I solid was weighed into a glass vial, 15 mL dimethyl carbonate was added, and then stirred at 5° C. for 17 hours to form a suspension. The suspension was centrifugated, and the separated solid was dried under vacuum at 50° C. for 3 hours to obtain a dry solid. 81.5 mg of the dry solid was weighed into a glass vial, 1 mL of isopropyl alcohol was added, and then stirred at room temperature for 14 hours to form a suspension. The formed suspension was centrifugated, and the separated solid was dried under vacuum at 40° C. for 4 hours to obtain Form CSV.

Example 5 Kinetic Solubility of Form CSIV, Form CSV and Form I

When solubility test is used to predict the in vivo performance of a drug, it is critical to simulate in vivo conditions as closely as possible. SGF can be used to simulate the condition in vivo and predict the effects of eating, thus solubility in this medium is closer to that in vivo.

Approximately 5-20 mg of Form CSIV and 5-20 mg Form CSV of the present disclosure were suspended into 2.0 mL of SGF to get suspensions. After equilibrated for 1 h and 24 h, concentrations (μg/mL) of these solutions were measured by UPLC. The results are listed in Table 4. WO2020010068A1 disclosed that the solubility of Form A (Form I in U.S. Pat. No. 9,266,861B2) in SGF is 1.1 μg/mL for both 1 hour and 24 hours.

TABLE 4

| Crystalline form | 1 hour Concentration (μg/mL) | 24 hours Concentration (μg/mL) |
|---|---|---|
| Form CSIV | 11.7 | 5.5 |
| Form CSV | 7.8 | 9.6 |

According to the results in Table 4, in SGF, Form CSIV and Form CSV have higher solubility than that of Form I.

Example 6 Physical and Chemical Stability of Form CSIV and Form CSV

Figure 6:
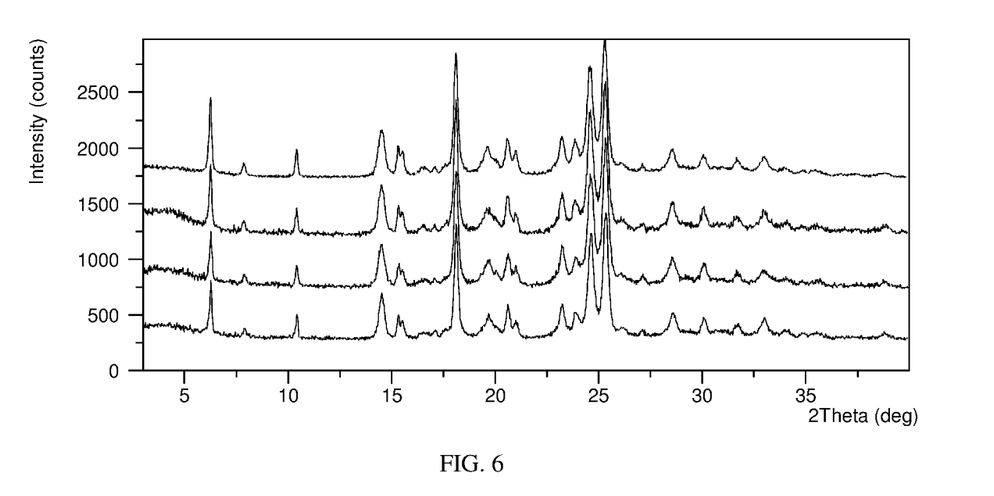
FIG. 6 shows an XRPD pattern overlay of Form CSIV before and after storage with sealed conditions (from top to bottom: initial, 25° C./60% RH for 6 months, 40° C./75% RH for 6 months, 60° C./75% RH for one month)

A certain amount of Form CSIV of the present disclosure was sealed up and stored under different conditions of 25° C./60% RH, 40° C./75% RH, and 60° C./75% RH. Crystalline form and chemical purity were checked by XRPD and HPLC, respectively. The results are shown in Table 5, and the XRPD overlay is shown in FIG. 6.

TABLE 5

| Conditions (sealed) | Time | Crystalline form | Purity |
|---|---|---|---|
| Initial | — | Form CSIV | 99.80% |
| 25° C./60% RH | 6 months | Form CSIV | 99.79% |
| 40° C./75% RH | 6 months | Form CSIV | 99.76% |
| 60° C./75% RH | One month | Form CSIV | 99.76% |

The results show that Form CSIV is stable for at least 6 months under 25° C./60% RH and 40° C./75% RH condition in sealed dish, and is stable for at least one month under 60° C./75% RH sealed condition. It can be seen that Form CSIV has good stability under long-term, accelerated and stress conditions.

Figure 7:
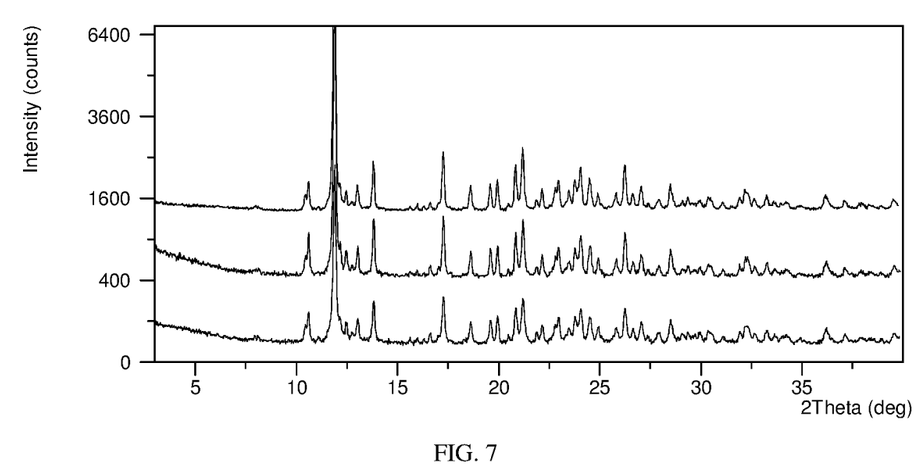
FIG. 7 shows an XRPD pattern overlay of Form CSV before and after storage under 40° C./75% RH (from top to bottom: initial, one month with open condition, one month with sealed condition)
Figure 8:
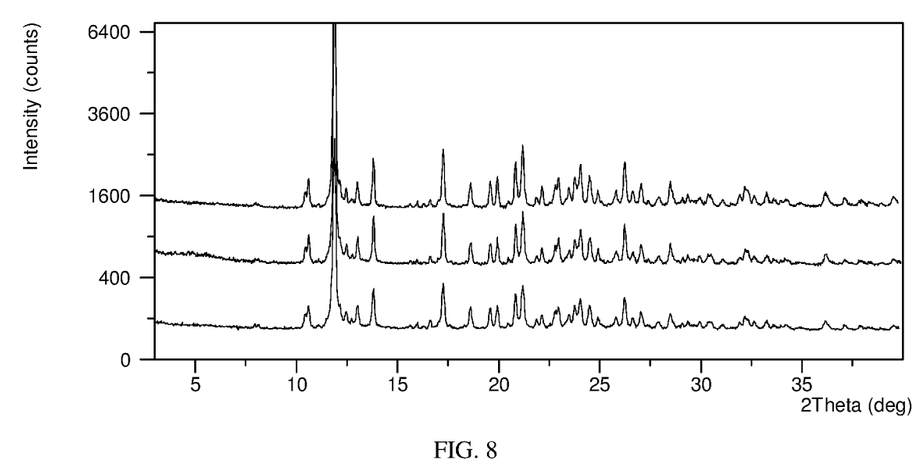
FIG. 8 shows an XRPD pattern overlay of Form CSV before and after storage under 60° C./75% RH (from top to bottom: initial, one week with open condition, one week with sealed condition)

A certain amount of Form CSV of the present disclosure was stored under different conditions of 40° C./75% RH and 60° C./75% RH in open and sealed dishes. Crystalline form and chemical purity were checked by XRPD and HPLC, respectively. The results are shown in Table 6, and the XRPD overlay are shown in FIG. 7 and FIG. 8.

TABLE 6

| Conditions | Time | Crystalline form | Purity |
|---|---|---|---|
| Initial |  | Form CSV | N/A |
| 40° C./75% RH (open) | One month | Form CSV | 99.81% |
| 40° C./75% RH (sealed) |  | Form CSV | 99.85% |
| 60° C./75% RH (open) | One week | Form CSV | 99.86% |
| 60° C./75% RH (sealed) |  | Form CSV | 99.87% |

The results show that Form CSV is stable for at least one months under 40° C./75% RH with open and sealed dishes, and is stable for at least one week under 60° C./75% RH with open and sealed dishes. It can be seen that Form CSV has good stability under accelerated and stress conditions.

Example 7 Physical Stability of Form CSV and Form I Upon Grinding

Form CSV and Form I were grounded manually for 5 minutes in a mortar. Crystalline forms before and after grinding were checked by XRPD. The results show that the crystalline state of Form CSV does not change before and after grinding, while Form I almost transform into amorphous after grinding. Compared with Form I, Form CSV has better physical stability upon grinding.

Example 8 Hygroscopicity of Form CSIV and Form CSV

Figure 9:
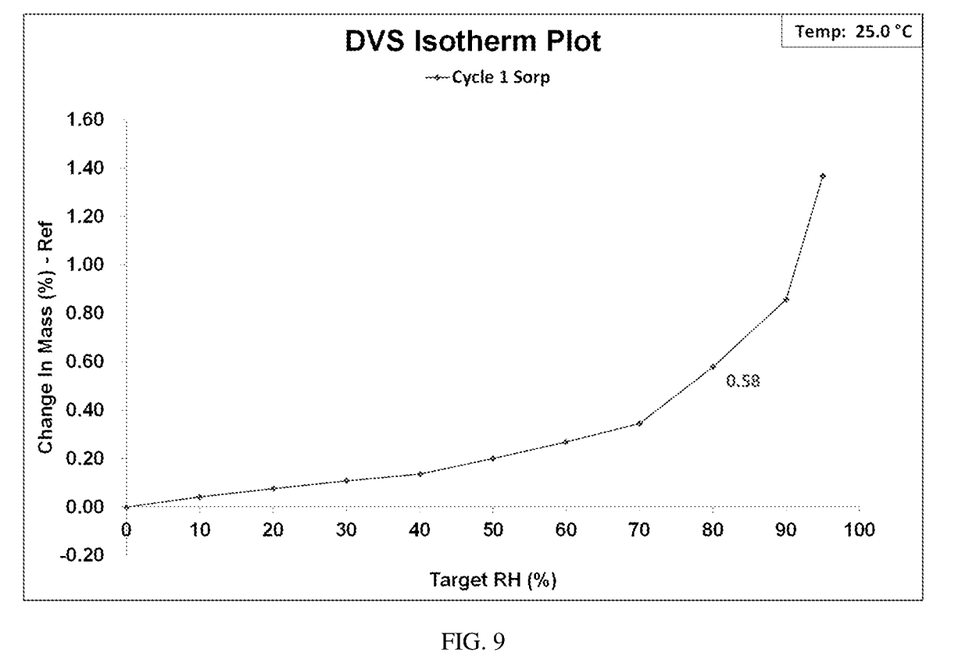
FIG. 9 shows a DVS curve of Form CSIV
Figure 10:
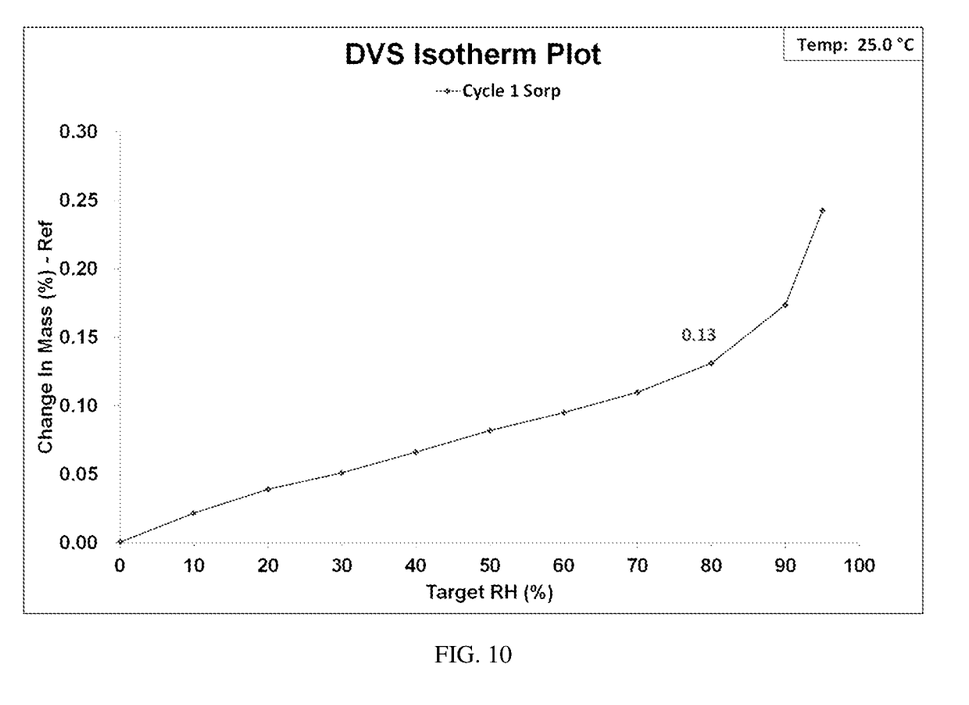
FIG. 10 shows a DVS curve of Form CSV

Dynamic vapor sorption (DVS) analyzer was applied to test hygroscopicity of Form CSIV and Form CSV with certain amount of samples. The weight gains at each relative humidity were recorded in a cycle of 0-95% RH. The results show that the weight gain of Form CSIV under 25° C./80% RH is 0.58%. Form CSIV is slightly hygroscopic, and the crystalline state remains unchanged before and after DVS. The weight gain of Form CSV under 25° C./80% RH is 0.13%. Form CSV is non hygroscopic or almost non-hygroscopic, and the crystalline state remains unchanged before and after DVS. The DVS curve of Form CSIV and Form CSV are shown in FIG. 9 and FIG. 10, respectively.

Description and definition of hygroscopicity (general notice 9103 drug hygroscopicity test guidelines in 2020 edition of Chinese Pharmacopoeia, test at 25° C.±1° C., 80% RH±2% RH. The definition of hygroscopicity in the 9th European Pharmacopoeia 5.11 is consistent with the Chinese Pharmacopoeia).

deliquescent: Sufficient water is absorbed to form a solution;

very hygroscopic: Increase in mass is equal to or greater than 15%;

hygroscopic: Increase in mass is less than 15% and equal to or greater than 2%;

slightly hygroscopic: Increase in mass is less than 2% and equal to or greater than 0.2%.

non hygroscopic or almost non hygroscopic: Increase in mass is less than 0.2%.

Example 9 Compressibility of Form CSIV

Figure 11:
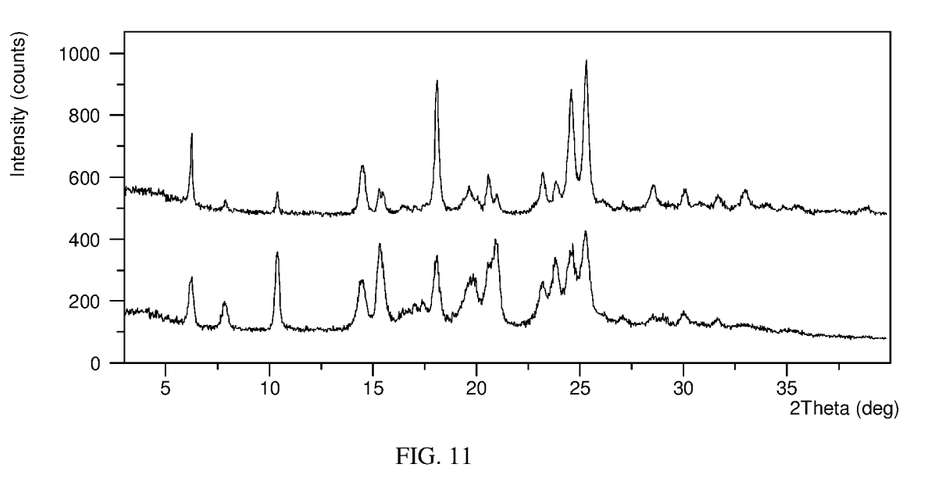
FIG. 11 shows an XRPD pattern overlay of Form CSIV before and after tableting (top: before tableting; bottom: after tableting)

ENERPAC manual tablet press was used for compression. 80 mg of Form CSIV and 80 mg of Form I were weighed and added into the dies of a φ6 mm round tooling, compressed at 10 kN manually, then stored at room temperature for 24 h. Diameter (D) and thickness (L) were tested with caliper. When elastic recovery is complete, hardness (H) was tested with an intelligent tablet hardness tester. Tensile strength of the powder was calculated with the following formula: T=2H/πDL. Under a certain force, the greater the tensile strength, the better the compressibility. The results are presented in Table 7. The XRPD pattern of Form CSIV before and after tableting is shown in FIG. 11.

TABLE 7

|  | Form I | | Form CSIV | |
| --- | --- | --- | --- | --- |
|  | 1 | 2 | 1 | 2 |
| Thickness (mm) | 2.11 | 2.00 | 2.12 | 2.12 |
| Diameter (mm) | 6.01 | 6.11 | 6.03 | 6.04 |
| Hardness (kg) | 8.7 | 7.9 | 28.3 | 27.7 |
| Tensile strength (MPa) | 0.44 | 0.41 | 1.41 | 1.38 |
| Average tensile strength (MPa) | 0.43 | | 1.40 | |

The results indicate that Form CSIV has better compressibility compared with Form I, and the crystalline state of Form CSIV remains unchanged before and after tableting.

Failure in hardness/friability test and tablet crack issue can be avoided due to better compressibility, making the preparation process more reliable, improving product appearance, promoting product quality. Better compressibility can increase the compression rate, thus further increases the efficiency of process. In addition, the crystalline form with good compressibility improves the feasibility of the process of direct compression and reduces the cost of research and production.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

The invention claimed is:

1. A crystalline form CSIV of Resmetirom, wherein the X-ray powder diffraction pattern comprises characteristic peaks at 2theta values of 6.3°±0.2°, 18.1°±0.2°, 20.6°±0.2°, 25.3°±0.2°, and 28.6°±0.2° using CuKα radiation, 2. The crystalline form CSIV of Resmetirom according to claim 1, wherein the X-ray powder diffraction pattern further comprises one or two characteristic peaks at 2theta values of 10.4°±0.2° and 24.6°±0.2° using CuKα radiation.

3. The crystalline form CSIV of Resmetirom according to claim 1, wherein the X-ray powder diffraction pattern further comprises one characteristic peak at 2theta values of 14.5°±0.2° using CuKα radiation.

4. The crystalline form CSIV of Resmetirom according to claim 1, wherein the X-ray powder diffraction pattern is substantially as depicted in FIG. 1.

5. A pharmaceutical composition, wherein said pharmaceutical composition comprises a therapeutically effective amount of crystalline form CSIV of Resmetirom according to claim 1, and pharmaceutically acceptable excipients.

6. A process for preparing crystalline form CSIV of Resmetirom according to claim 1, wherein the process comprises suspending Resmetirom solid in acetonitrile, stirring, separating the obtained solid and drying to obtain crystalline form CSIV.

7. The process according to claim 6, wherein said drying temperature is 50-100° C.

8. A method of activating THR-β, comprising administering to a subject in need thereof a therapeutically effective amount of crystalline form CSIV of Resmetirom according to claim 1.

9. A method for treating NASH and HeFH, comprising administering to a subject in need thereof a therapeutically effective amount of crystalline form CSIV of Resmetirom according to claim 1.

* * * * *